United States Patent
Girardi et al.

(10) Patent No.: US 12,076,302 B2
(45) Date of Patent: Sep. 3, 2024

(54) DERMATOLOGIC TOPICAL APPLICATIONS OF ROR GAMMA AND ROR GAMMA-T INHIBITORS FOR THE PREVENTION OF SKIN CANCER DEVELOPMENT

(71) Applicant: Yale University, New Haven, CT (US)

(72) Inventors: Michael Girardi, Madison, CT (US); Julia Lewis, Clinton, CT (US)

(73) Assignee: Yale University, New Haven, CT (US)

( * ) Notice: Subject to any disclaimer, the term of this patent is extended or adjusted under 35 U.S.C. 154(b) by 695 days.

(21) Appl. No.: 17/276,800

(22) PCT Filed: Sep. 17, 2019

(86) PCT No.: PCT/US2019/051482
§ 371 (c)(1),
(2) Date: Mar. 16, 2021

(87) PCT Pub. No.: WO2020/061024
PCT Pub. Date: Mar. 26, 2020

(65) Prior Publication Data
US 2021/0353568 A1 Nov. 18, 2021

Related U.S. Application Data

(60) Provisional application No. 62/733,060, filed on Sep. 18, 2018.

(51) Int. Cl.
*A61K 31/165* (2006.01)
*A61K 9/00* (2006.01)
*A61K 45/06* (2006.01)

(52) U.S. Cl.
CPC .......... *A61K 31/165* (2013.01); *A61K 9/0014* (2013.01); *A61K 45/06* (2013.01)

(58) Field of Classification Search
CPC .... A61K 31/165; A61K 9/0014; A61K 45/06; A61K 31/4535; A61P 35/04; A61P 35/00; C12N 5/0602; C12N 5/0625; C12N 5/0629; C12N 5/0693
See application file for complete search history.

(56) References Cited

U.S. PATENT DOCUMENTS

2018/0085348 A1* 3/2018 Chen .................... A61K 31/713

FOREIGN PATENT DOCUMENTS

WO    WO-2012176015 A1 * 12/2012 ............. A61K 31/22
WO    WO 2015/140722 A1    9/2015

OTHER PUBLICATIONS (Slominski, AT et al.) Characterization of a new pathway that activates lumisterol in vivo to biologically active hydroxylumisterols. Scientific Reports. Sep. 12, 2017, vol. 7, No. 1; pp. 1-17; abstract; p. 10, 3rd paragraph.*

(Continued)

*Primary Examiner* — Deborah D Carr
(74) *Attorney, Agent, or Firm* — Wolf, Greenfield & Sacks, P.C.

(57) ABSTRACT

Described herein are methods and compositions useful to reduce (partially/inhibit or completely—prevent) skin cancer development in an individual in need thereof.

16 Claims, 8 Drawing Sheets

(56) References Cited

OTHER PUBLICATIONS (Slominski, AT et al.) ROR(alpha] and ROR[gamma] are expressed in human skin and serve as receptors for endogenously produced noncalcemic 20-hydroxy- and 20,23-dihydroxyvitamin D. FASEB Journal. Jul. 2014, Epub Mar. 25, 2014, vol. 28, No. 7; pp. 2775-2789; abstract; p. 7, 6th paragraph.*

International Search Report and Written Opinion, mailed Dec. 2, 2019, for Application No. PCT/US2019/051482.

International Preliminary Report on Patentability, mailed Apr. 1, 2021, for Application No. PCT/US2019/051482.

Hahn et al., Mutations of the human homolog of *Drosophila* patched in the nevoid basal cell carcinoma syndrome. Cell. Jun. 14, 1996;85(6):841-51.

Johnson et al., Human homolog of patched, a candidate gene for the basal cell nevus syndrome. Science. Jun. 14, 1996;272(5268):1668-71.

Situm et al., The role of UV radiation in the development of basal cell carcinoma. Coll Antropol. Oct. 2008;32 Suppl 2:167-70.

* cited by examiner

FIG. 2A

DERMATOLOGIC TOPICAL APPLICATIONS OF ROR GAMMA AND ROR GAMMA-T INHIBITORS FOR THE PREVENTION OF SKIN CANCER DEVELOPMENT

RELATED APPLICATIONS

This application is a national stage filing under 35 U.S.C. § 371 of International Patent Application Serial No. PCT/US2019/051482, filed Sep. 17, 2019, which was published under PCT Article 21(2) in English and claims the benefit under 35 U.S.C. § 119(e) of U.S. provisional application No. 62/733,060, filed Sep. 18, 2018, each of which is incorporated by reference herein in its entirety.

GOVERNMENT FUNDING

This invention was made with government support under CA102703 awarded by National Institutes of Health. The government has certain rights in the invention.

BACKGROUND

Skin cancers (including basal and squamous cell carcinoma, and melanoma) are the most common cancers in the world. Several groups of people are at greater risk than others. These include those who are fair skinned, red haired, freckled; have blonde hair, blue eyes; or exhibit other melanocortin1 receptor (Mc1r) deficient states; those with a history of photodamage; those with a personal history or family history of pre-cancerous or skin cancerous lesions; those with known specific genetic polymorphisms that predispose to skin cancer; those with frank genetic disorders that predispose individuals/populations to higher risks of skin cancer, including basal cell nevus syndrome, xeroderma pigmentosum, epidermolysis bullosa, or oculocutaneous albinism; those with familial atypical mole-melanoma syndrome; and organ and peripheral blood stem cell transplant patients taking immune suppressive medications.

SUMMARY

Described herein are methods and compositions useful to reduce (partially/inhibit or completely/prevent) skin cancer development. Described in one embodiment are dermatologic (skin) topical applications of RORC inhibitors, including dermatologic topical applications of RORγ (also referred to herein as RORg and ROR gamma) inhibitors, dermatologic topical applications of RORγ-t (also referred to herein as RORγt, RORg-t and ROR gamma-t) inhibitors, dermatologic topical applications of inhibitors of both RORγ and RORγt, and dermatologic topical applications of a combination of one or more RORγ inhibitor and one or more RORγ-t inhibitor for the inhibition (e.g., prevention or reduction) of skin precancerous lesion or skin cancer development; such inhibitors are useful for direct inhibition and local immunoregulation of cutaneous carcinogenesis. The methods described herein comprise repetitive (repeated) dermatologic topical applications of RORγ inhibitors; repetitive (repeated) dermatologic topical applications of RORγ-t inhibitors; repetitive (repeated) dermatologic topical applications of inhibitors that inhibit both RORγ and RORγt; repetitive (repeated) dermatologic topical applications of a combination of one or more RORγ inhibitor(s); repetitive (repeated) dermatologic topical applications of a combination of one or more RORγ-t inhibitor(s); and repetitive (repeated) dermatologic topical applications of a combination of one or more inhibitors that inhibit both RORγ and RORγt for sufficient time and dose to reduce (partially or completely/prevent) the incidence of skin cancer development. RORC (RAR-related orphan receptor C) is the gene that encodes both ROR gamma and ROR gamma-t isoforms. Inhibitors that inhibit both RORγ and RORγt can be (1) a combination of one or more inhibitor(s) of RORγ and one or more inhibitor(s) of RORγ-t or (2) one or more inhibitor(s) that inhibit both RORγ and one or more inhibitor(s) of RORγ-t (the same inhibitor inhibits both RORγ and RORγ-t). RORC products include, but are not limited to, RORγ and RORγ-t.

One aspect of the disclosure is a method of inhibiting development, in an individual, also referred to as a subject, (e.g., a human) of keratinocyte-derived malignancy characterized by mutations in p53 gene, comprising applying repetitively at least one topical inhibitor of an RORC product to skin in sufficient concentration and over sufficient time to reduce local production, such as by innate lymphoid cells, T cells, and/or other immune cells, of at least one factor that drives keratinocyte transformation and mutant clonal expansion. In the method, the at least one (one or more) factor is IL-17A, IL-17F, IL-22 or IL-36a.

Another embodiment is a method of inhibiting (partially/reduce or completely/prevent) UV-induced cutaneous carcinogenesis in an individual, comprising applying topically and repetitively to skin of the individual at least one (one or more) inhibitor of RORγ in sufficient concentration and for sufficient length of time to have the desired effect, which can include, for example, inhibition of any or all of the following: keratinocyte genotoxicity, epidermal proliferation and dedifferentiation and mutant (e.g., p53) keratinocyte clonal expansion; at least one (one or more) inhibitor of RORγ-t in sufficient concentration and for sufficient length of time to have the desired effect, which can include, for example, inhibition of any or all of the following: keratinocyte genotoxicity, epidermal proliferation and dedifferentiation and mutant (e.g., p53) keratinocyte clonal expansion; or at least one (one or more) inhibitor of RORγ and at least one (one or more) inhibitor of RORγ-t in sufficient concentration and for sufficient length of time to in sufficient concentration and for sufficient length of time to have the desired effect, which can include, for example, inhibition of any or all of the following: keratinocyte genotoxicity, epidermal proliferation and dedifferentiation and mutant (e.g., p53) keratinocyte clonal expansion.

A further embodiment is a method of inhibiting (partially/reduce or completely/prevent) actinic keratosis and squamous cell carcinoma in an individual, comprising applying repetitively at least one topical inhibitor of an RORC product (e.g., at least one (one or more) inhibitor of RORγ, at least one (one or more) inhibitor of RORγ-t; or at least one (one or more) inhibitor of RORγ and at least one (one or more) inhibitor of RORγ-t) to the individual's skin in sufficient concentration and over sufficient time to reduce (partially or completely/prevent) UV-induced cutaneous carcinogenesis. In some embodiments, an inhibitor of an RORC product is an inhibitor of both RORγ and RORγ-t (one inhibitor inhibits both RORγ and RORγ-t).

A further embodiment is a method of reducing (partially or completely/preventing) facilitation of chronic UV-induced cutaneous carcinogenesis in an individual, comprising applying repetitively at least one topical inhibitor of an RORC product (e.g., at least one (one or more) inhibitor of RORγ; at least one (one or more) inhibitor of RORγ-t; or at least one (one or more) inhibitor of RORγ and at least one (one or more) inhibitor of RORγ-t) to the individual's skin in sufficient concentration and over sufficient time to reduce (partially or completely) UV-induced cutaneous carcinogenesis.

The concentration of inhibitor(s), the number of times inhibitor(s) (e.g., the number of applications per day) are applied and the length of time (e.g., the number of days, weeks, months) the at least one inhibitor(s) are applied will vary and can be determined using known methods and with reference to such factors as characteristics of an individual on whom it will be applied (an individual in need thereof), such as fair skin, red hair, freckled skin; blonde hair, blue eyes; a history of photodamage; a personal history or family history of pre-cancerous or skin cancerous lesions; known specific genetic polymorphisms that predispose to skin cancer; genetic disorders that pre-dispose individuals/populations to higher risks of skin cancer, including basal cell nevus syndrome, xeroderma pigmentosum, epidermolysis bullosa, or oculocutaneous albinism; those with familial atypical mole-melanoma syndrome; and consumption of immune suppressive medications.

In the methods, the concentration of ROR inhibitors (the concentration of RORγ inhibitors; the concentration of RORγt inhibitors; the concentration of RORγ inhibitors and RORγt inhibitors in combinations of RORγ inhibitors and RORγt inhibitors) can be, for example, from about 10 mg/ml to about 100 mg./ml. or, for example, about 1% inhibitor (in solution, e.g. 60% ethanol, 40% water, or other topical formulations, including cream, ointment, foam, sprays, and gels, including anhydrous and hydrous) or, for example, 1% (0.1 to 10%) in a preparation, including 1% (0.1 to 10%) in a cream preparation (about 100 micromolar range) and the at least one topical inhibitor is applied repeatedly, such as once monthly (e.g., for at least 4 months), weekly (e.g., for at least 4 weeks), or daily (e.g., for at least one week). In each embodiment of the method, RORγ inhibitors; RORγt inhibitors; or combinations of RORγ inhibitors and RORγt inhibitors can be applied in combination with other agents, such as anti-oxidant(s), sunscreen filter agent(s), anti-aging agent(s), anti-inflammatory agent(s), triplet state preventer(s), and triplet state quencher(s).

Examples of RORC inhibitors are small molecules, such as diphenylpropanamide compounds (e.g., ML209, also referred to as compound 4n, useful as a selective RORCγ inhibitor), RORCi, digoxin, ursolic acid, SR2211, TMP778, GSK805 and GSK2981278.

Also the subject of this invention are compositions useful in the methods, such as compositions comprising at least one RORγ inhibitor; at least one RORγt inhibitor; or a combination of at least one RORγ inhibitor and at least one RORγt inhibitor, alone or in combination with other agents, such as at least one anti-oxidant(s), at least one sunscreen filter agent(s), at least one anti-aging agent(s), at least one anti-inflammatory agent(s), at least one triplet state preventer(s), or at least one triplet state quencher(s). The compositions can comprise, in addition to the at least one RORγ inhibitor; at least one RORγt inhibitor; or a combination of at least one RORγ inhibitor and at least one RORγt inhibitor, a combination of two or more additional agents (e.g., a combination of at least two or more of the following: at least one anti-oxidant(s), at least one sunscreen filter agent(s), at least one anti-aging agent(s), at least one anti-inflammatory agent(s), at least one triplet state preventer(s), or at least one triplet state quencher(s)). Each RORC inhibitor, whether administered alone or in combination with a second, different RORC inhibitor is present in the composition at a concentration of from about 10 mg./ml. to about 100 mg./ml. or about 1% in solution, e.g. 60% ethanol, 40% water, or other topical formulations including cream, ointment, foam, sprays, and gels; including anhydrous and hydrous). From about 1 $mg/cm^2$ to 10 $mg/cm^2$ RORC inhibitor is applied per application.

These methods and compositions are useful, for example, to decrease the incidence of skin cancer in at-risk individuals, reduce the severity of skin cancer and decrease the number of procedures (e.g. surgery) needed over a person's life and, as a result, for example, decrease risk of death from skin cancer, improve an individual's quality of life, and decrease healthcare costs.

BRIEF DESCRIPTION OF THE DRAWINGS

FIG. 2A illustrates the phenotype of RORC+ skin innate lymphoid cells (ILC) in B6.TCR--/-δ-/- mice. Cells were gated on CD45+Thy1+LIN- for flow cytometry.

DETAILED DESCRIPTION

Figure 1A:
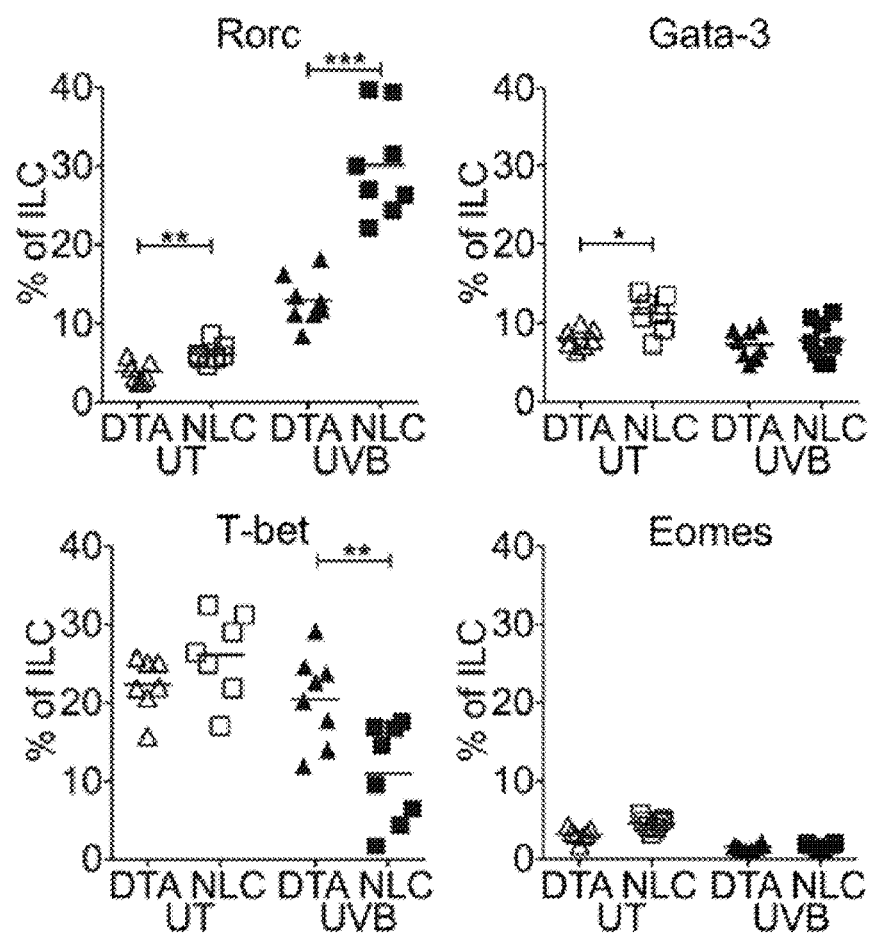
FIG. 1A is a series of graphs demonstrating that the expression of RORC, an immune cell differentiation factor, is markedly elevated in the skin of B6.TCRβ-/-δ-/- mice after ultraviolet B (UVB) light exposure, and in the presence of Langerhans cells (NLC), the dendritic immune cell of the epidermis. The other immune cell differentiation factors tested (Gata-3, T-bet, Eomes) did not show augmented expression with UVB exposure.

Non-melanoma skin cancers (NMSCs), basal cell carcinoma (BCC) and squamous cell carcinoma (SCC) are keratinocyte-derived malignancies that together comprise the most prevalent form of cancer in the United States. Squamous cell carcinomas arise from damaged epidermal basal and folliculo-infundibular keratinocytes (KC), which most often evolve first into pre-cancerous actinic keratoses (AKs); they affect more than 50 million Americans. Chronic ultraviolet (UV) light exposure has been implicated as the major environmental risk factor for development of actinic keratoses and squamous cell carcinoma. Both types of neoplasm harbor frequent mutations in the master cell cycle regulator p53 gene. As described, Langerhans cells (LC) have a critical role in cutaneous carcinogenesis, which definitively demonstrates that LC exert major influences in stimulating both KC genotoxicity and facilitating tumor promotion.

Without wishing to be bound by theory, the results described support a role for LC as detectors of physical and chemical epidermal perturbation and as providers of effector functions for the stimulation of KC genotoxicity (the hallmark of transformation) and proliferation and dedifferentiation (the hallmarks of dysplasia and mutant clonal expansion). Described herein are novel paradigms that relate LC regulation of the epidermal stress response and IL-22-producing innate lymphoid cells (ILC) and T cells to UV-induced carcinogenesis. For conditions of physiologic epidermal perturbation, under this construct, LC are poised to detect and respond to keratinocyte damage, eliciting precise, localized responses. When such epidermal perturbation leads to DNA-damaging exposure (e.g. chemical mutagen, ultraviolet radiation), resulting in KC acquisition of mutations that silence tumor-suppressor genes and/or constitutively activate oncogenes to support proliferation and resistance to apoptosis, a clonal expansion of the mutated KC ensues. In this way, tumor promotion usurps the normal physiological response of LC, and chronic UV exposure and stressed KC stimulate LC to produce factors that drive KC transformation and mutant clonal expansion. Results from multiple models of cutaneous carcinogenesis have shown that the net effect of these activities on the rates of clonal formation, clonal expansion, and eventual tumor outgrowth is unequivocally dependent on the presence of LC. Described herein is identification of the underlying mechanisms and translational targeting of such mechanisms. This involves elucidating the effector mechanisms underlying LC facilitation of chronic UV-induced cutaneous carcinogenesis, identifying key sensor components mediating LC facilitation of chronic UV-induced cutaneous carcinogenesis, and investigating the potential to translationally inhibit LC-mediated mechanisms that facilitate cutaneous malignancy. Described herein is an innovative strategy, including methods that permit the selective repopulation of LCs from precursor-rich fetal tissues, which can be used to elucidate the mechanisms by which LCs facilitate chronic UV-induced keratinocyte genotoxicity, epidermal proliferation and dedifferentiation, and mutant p53 KC clonal expansion.

Figure 1B:
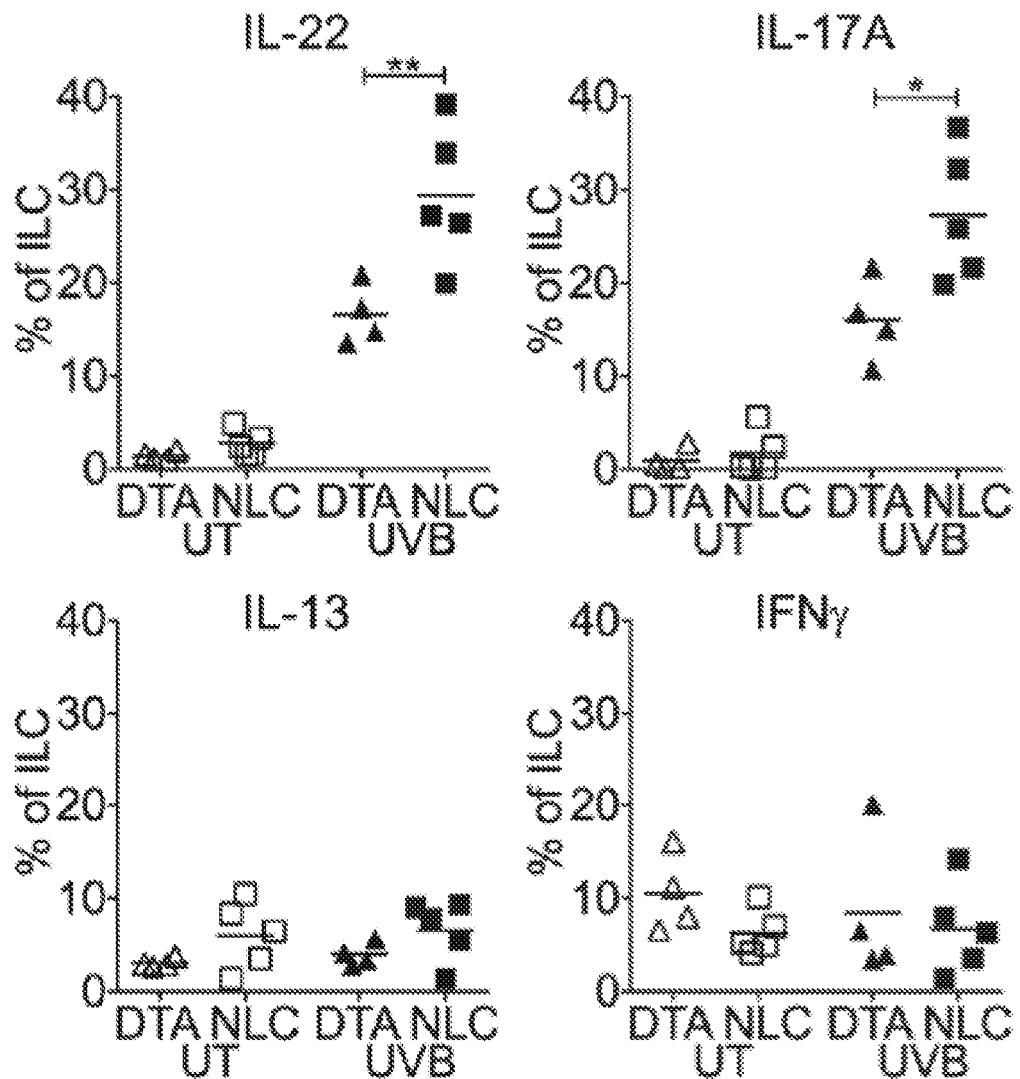
FIG. 1B is a series of graphs demonstrating that the cytokine products of RORγt+ cells, IL-22 and IL-17, are significantly elevated in the skin of B6.TCRβ-/-δ-/- mice after ultraviolet B (UVB) light exposure, and in the presence of Langerhans cells (NLC). The cytokine products of the other differentiation cell factors, IL-13 and IFNγ showed no such augmented expression with UVB exposure.
Figure 1C:
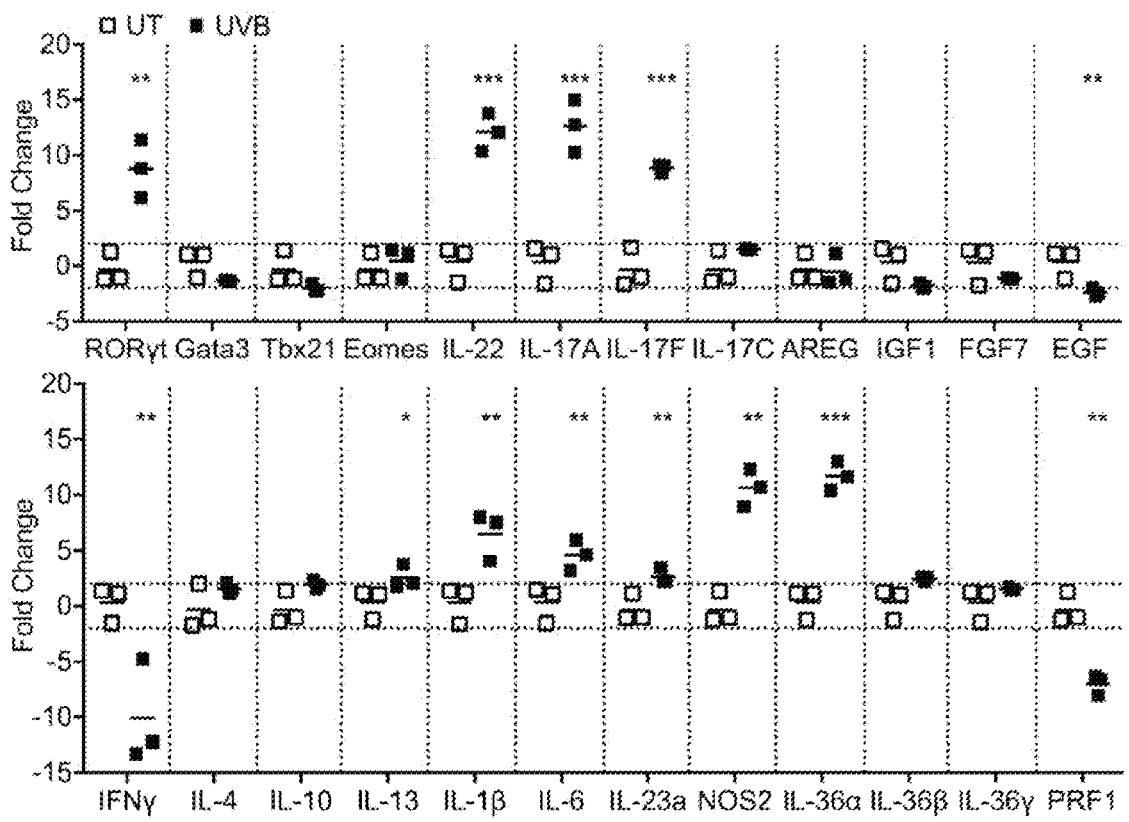
FIG. 1C provides qRT-PCR results, revealing essentially the same pattern shown in FIGS. 1A-1B in response to UVB exposure in the skin of B6.TCR B6.TCRβ-/-δ-/- mice.
Figure 2A:
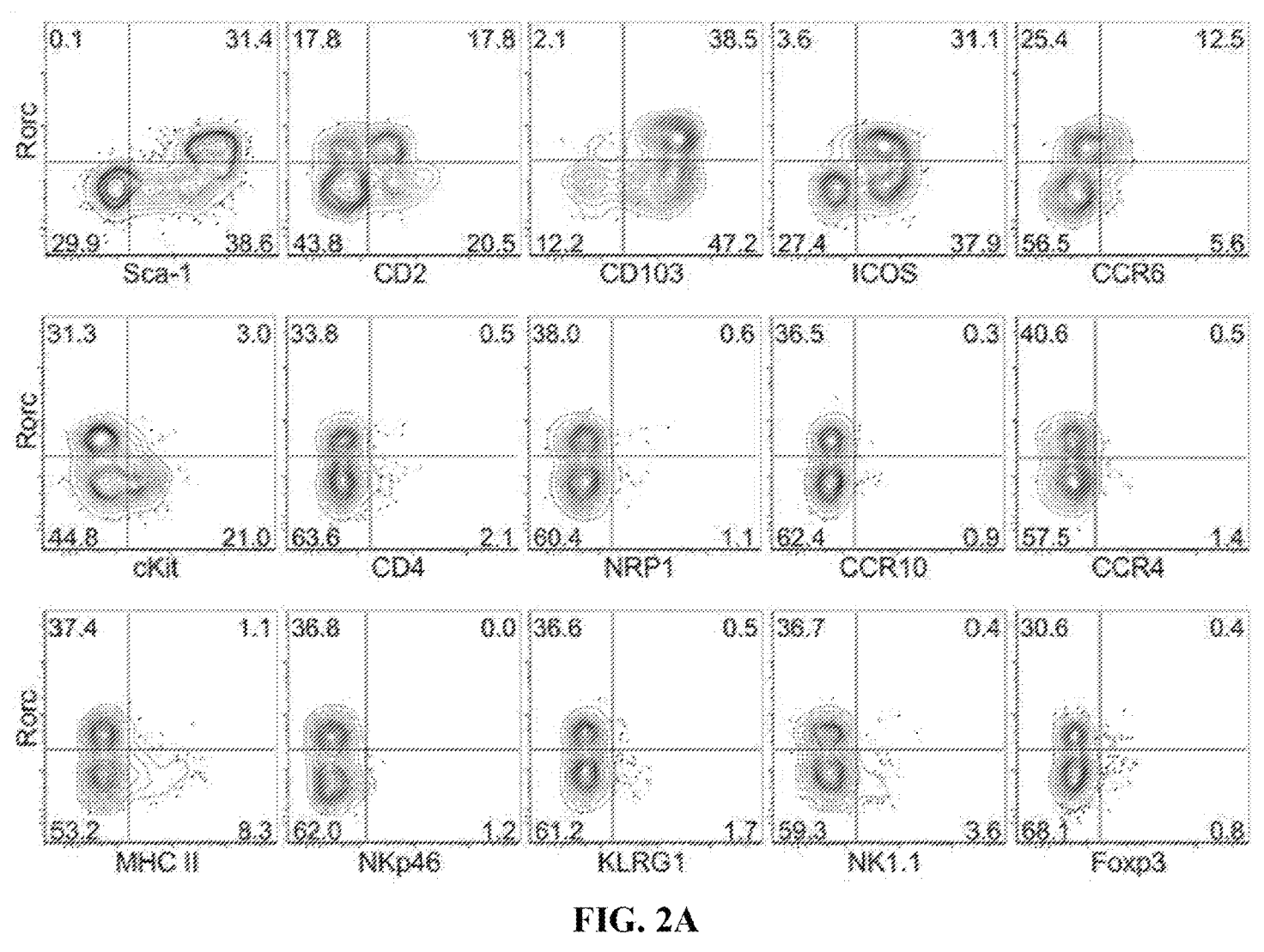
Figure 2B:
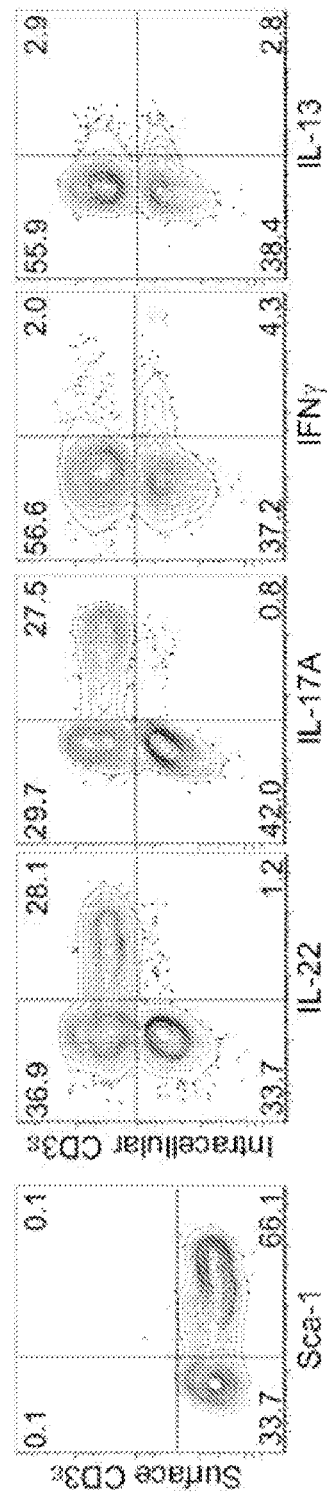
FIG. 2B presents flow cytometry plots demonstrating that IL22+ and IL17A+ cells are intracellular CD3e+, while IL-13 and IFNγ are not.
Figure 2C:
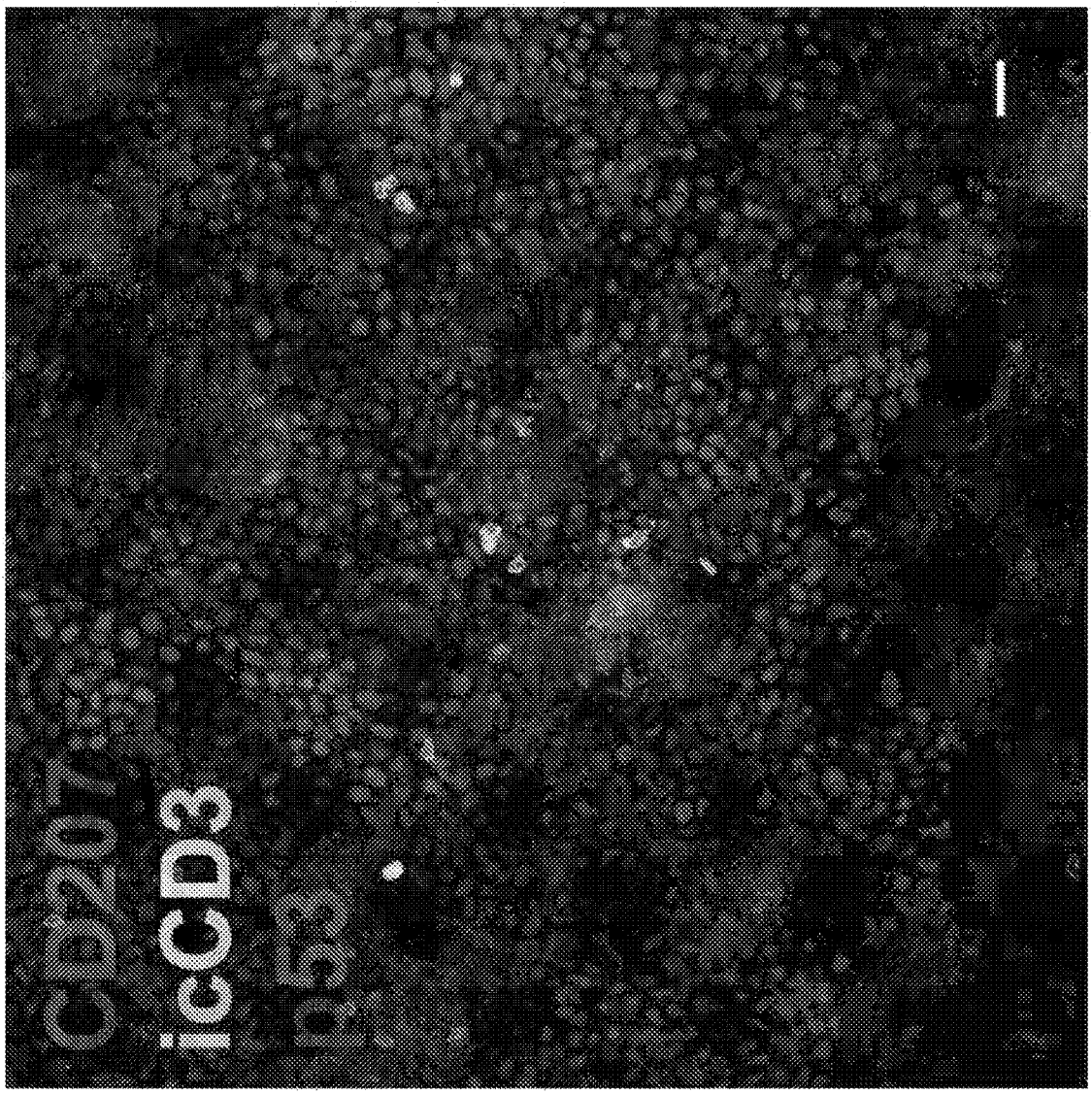
FIG. 2C shows intracellular CD3e+ cells in chronic UVB exposed epidermis.
Figure 2D:
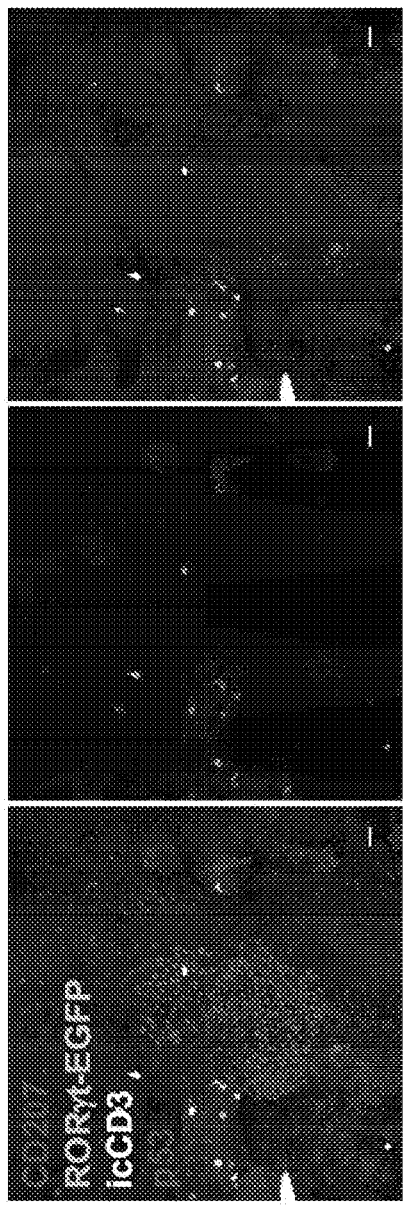
FIG. 2D shows that, in B6.TCRβ-/-δ-/-.RORγt-EGFP T cell-deficient reporter mice, epidermal EGFP+ cells are largely intracellular CD3e+.
Figure 3A:
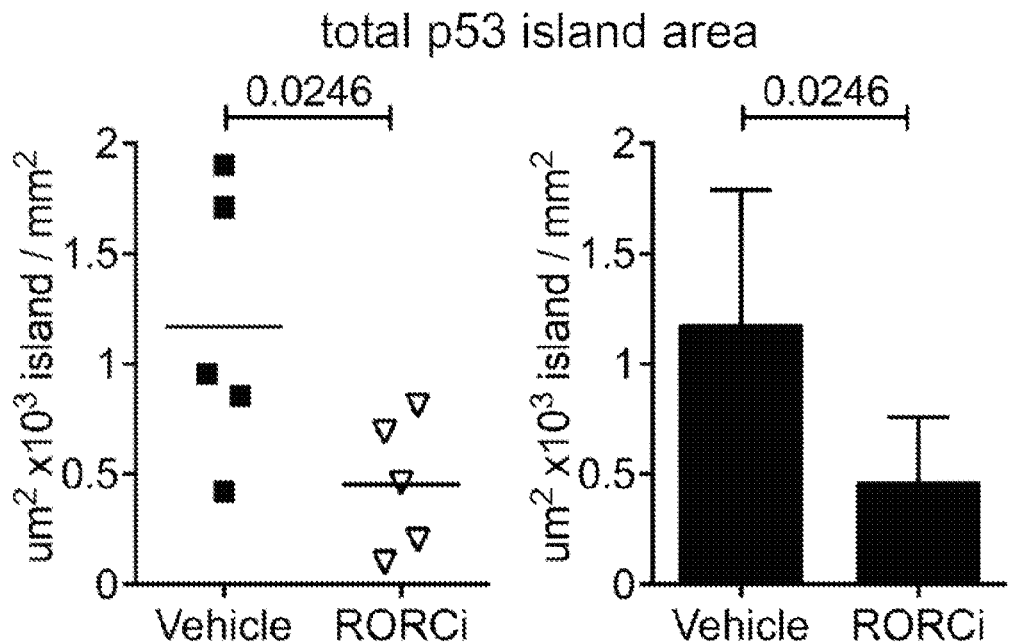
FIG. 3A illustrates the total p53 "island" area formed after exposure to UVB in mice. RORCi, an inhibitor of RORγ and RORγt, was applied to the experimental group, and was found to decrease the mutant p53 cells/per island by approximately 65% after two weeks of application.
Figure 3B:
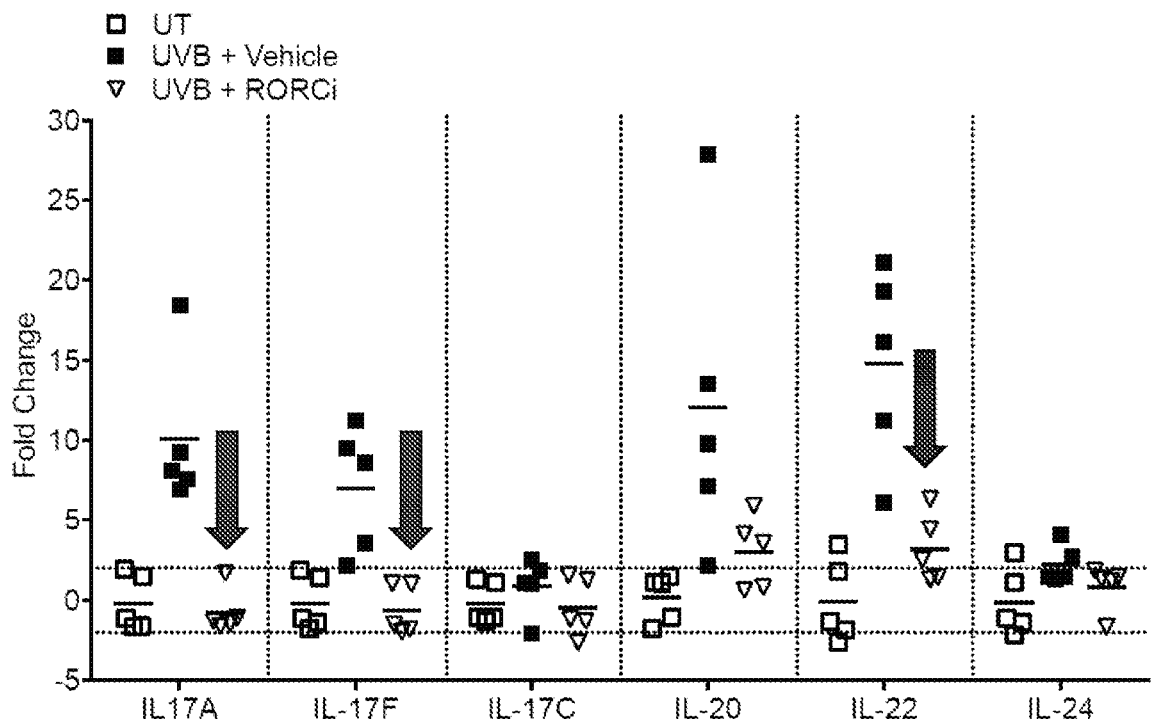
FIG. 3B illustrates that RORCi repressed the expression of the key cytokines/growth factors produced by RORC+ immune cells (arrows).

In particular, it was found that expression of RORC, an immune cell differentiation factor, and its cytokine products were significantly increased in the skin of B6.TCRβ−/−δ−/− mice exposed to ultraviolet B (UVB) light in the presence of LC (FIGS. 1A-1C). The same marked increase was not observed in other immune cell differentiation factors tested. Further, it was found that RORC+ skin innate lymphoid cells (ILC) were CD103+ and ICOS+ (FIG. 2A) and that IL-22- and IL-17A-positive cells are intracellular CD3e+ (FIG. 2B). Intracellular CD3e+ cells were found in chronic UVB exposed epidermis (FIG. 2C), and, in RORγt-deficient mice, it was found that epidermal EGFP+ cells were largely intracellular CD3e+ (FIG. 2D). Taken together, this data pointed to RORC as a therapeutic and/or preventative target for keratinocyte-derived malignancies. As shown in FIGS. 3A and 3B, application of RORCi, an inhibitor of RORγ and RORγt, markedly decreased mutant keratinocyte clonal expansion and repressed expression of key cytokines and growth factors produced by RORC+ immune cells in mice after exposure to UVB. These results show the reduction, partial or total (e.g., prevention) of microscopic pre-cancerous skin lesions in sun-damaged skin. The results (novel dataset) show, for example, the fuller elucidation of the immune pathways affected by RORγ and/or RORγt inhibition, specifically the inhibition of local production of IL-17A and F, IL-22, and IL-36a (FIG. 3B), which are implicated in mutant keratinocyte clonal expansion and skin cancer development, and the markedly decreased mutant keratinocyte clonal expansion in RORγt-deficient and IL-22-deficient mice.

Also described is the specific inhibition of RORγt (with little or no (without) specific inhibition of RORγ). Results support the benefit of such specific inhibition in limiting mutant keratinocyte clonal expansion. Such specificity should optimize the benefit to risk ratio (safety and performance) of using RORγt-specific inhibitors.

Provided herein, in some embodiments, are methods and compositions (that inhibit (e.g., prevent or reduce) the development of a keratinocyte-derived malignancy (e.g., UV-induced cutaneous carcinogenesis, actinic keratosis, basal cell carcinoma, squamous cell carcinoma) characterized by mutations in the p53 gene using one or more RORC inhibitors (RORγ and/or RORγt inhibitors). Accordingly, in some embodiments, the methods and compositions provided herein inhibit (e.g., prevent or reduce) skin cancer development.

RORC Inhibitors (RORγ and/or RORγt Inhibitors)

A key immune pathway drives clonal expansion of mutated keratinocytes. At the root of this pathway are the differentiation factors and gene expression regulators, RORγ and RORγt, both of which are encoded by the gene RORC. RORC (RAR-related orphan receptor C; RefSeqGene NG_029118.1; gene ID: 6097) is a member of the nuclear receptor gene superfamily and encodes two isoforms: RORγ and RORγt. As described herein, application of RORγ and/or RORγt inhibitors prevents or reduces the development of keratinocyte-derived malignancies. The phrases "RORγ and/or RORγt inhibitors" and "RORC product inhibitor(s)" as used herein, encompass three types of RORC product inhibitors: RORγ inhibitors, RORγt inhibitors, and inhibitors that inhibit both RORγ and/or RORγt.

RORγ and/or RORγt inhibitors are known in the art and are commercially available. Examples include, but are not limited to, small molecules, such as diphenylpropanamide compounds (e.g., ML209, also referred to as compound 4n, a selective RORC inhibitor), RORCi, benzenesulfoamide (T0901317), digoxin, imidazopyridine (cpd 1), ursolic acid, S18-000003, SR1001, SR2211, tetrahydroquinoline, TMP778, VPR-66, GSK805 and GSK2981278.

The concentration of RORγ inhibitors, RORγt inhibitors or combinations of RORγ inhibitors and RORγt inhibitors can vary, depending on such factors as status of the skin/extent of skin damage; age; gender; and/or size of an individual being treated.

Methods of Treatment

Provided herein are method of preventing or reducing the severity of pre-cancerous skin lesions (actinic keratosis) and/or skin cancer (including squamous cell carcinoma, SCC; basal cell carcinoma, BCC; melanoma; Merkel cell carcinoma, MCC) or preventing the development of skin cancer through the repetitive topical application of RORγ and/or RORγt inhibitors. The pre-cancerous skin lesions and skin cancers described herein may result from exposure to ultraviolet (UV) radiation. Most UV exposure in humans in due to sun exposure; however, other sources, such as tanning beds and welding torches, also provide UV exposure. There are three types of UV radiation: UVA, UVB, and UVC. UVA radiation has been linked to long-term skin damage (e.g., wrinkles) and UVC radiation reacts with ozone and does not reach the ground. UVB radiation is most commonly associated with skin cancer; UVB rays cause sunburn and can damage DNA in skin cells directly (e.g., mutations in p53). In some embodiments, the pre-cancerous lesion(s) and/or skin cancer result from UV exposure, such as UVB exposure.

Squamous cell carcinoma (SCC) is an invasive malignant neoplasm of epidermal keratinocytes and is usually related to ultraviolet radiation exposure. In the United States, an estimated 700,000 cases of SCC are diagnosed every year.

Basal cell carcinoma (BCC) (also known as Gorlins Syndrome) is an autosomal dominant disorder that results from mutations in the p53 and/or PTCH genes. Hahn et al., Cell 1996; 85(6):841-851; Johnson et al., Science 1996; 272 (5268):1668-1671. The PTCH gene is involved in the hedgehog signal transduction pathway and Gorlins syndrome. UV radiation is the most important risk factor in the development of BCC, as short-wavelength UVB radiation is thought to play a greater role in BCC formation than long-wavelength UVA radiation. Situm et al., Coll Antropol. 2008 October; 32 Suppl 2:167-170.

BCC is the most common cancer in the United States, accounting for 75% of all skin cancers. With an incidence of 1 in 19,000, development of basal cell carcinomas is one of the major criteria for diagnosis and cause of morbidity and mortality. Evans et al., Am Journal of Medical Genetics A. 2010; 152:327-332. Basal carcinoma burden may vary from few to thousands of lesions and appear clinically and histopathologically similar to sporadic basal cell carcinomas, with similar rates of invasion and metastasis. Metastases are rare; tumors may locally invade surrounding tissues and bone.

Merkel Cell Carcinoma (MCC) is a rare aggressive neuroendocrine carcinoma located between the dermal-epidermal junction. MCC is caused by chronic exposure to ultraviolet radiation. In 2007, approximately 1,500 new cases of MCC were reported in the United States. MCC is also referred to as Toker tumor, primary small cell carcinoma of the skin, primary cutaneous neuroendocrine tumor and malignant trichodiscoma.

Actinic Keratosis (AK) is pre-cancerous lesion that if left untreated, may turn into squamous cell carcinoma. Actinic keratosis is caused by chronic exposure to ultraviolet radiation. It is also referred to as solar keratosis and senile keratosis.

Therefore, provided herein include inhibiting the development of (e.g., treating or preventing) any of the skin cancers described above by administering repetitive topical applications of one or more (at least one) ROR inhibitor, which can be (a) one or more (at least one) RORγ inhibitor(s), (b) one or more (at least one) RORγt inhibitor (s), (c) one or more (at least one) inhibitor(s) that inhibit both RORγ and RORγt, or (d) two or more types of RORC inhibitors to the skin of an individual in need thereof.

The phrase "skin cancer development" includes, but is not limited to, occurrence of skin cancer, growth of clinically and/or histologically evident skin lesions that are considered pre-cancerous (e.g., actinic keratosis) or cancerous (e.g., basal cell carcinoma, squamous cell carcinoma) and further progress of skin cancer once it is established. The phrase "inhibiting skin cancer development" or "inhibiting development of a keratinocyte-derived malignancy" includes, but is not limited to, prevention of the occurrence of/limiting the extent of occurrence of skin cancer; the growth of clinically and/or histologically evident skin lesions that are considered precancerous (e.g. actinic keratoses) or cancerous (e.g. basal cell carcinoma, squamous cell carcinoma); and further progress of skin cancer once it is established. For example, the area of skin cancer precancerous or cancerous lesions is reduced 5%, 10%, 15%, 20%, 25%, 30%, 35%, 40%, 45%, 50%, 55%, 60%, 65%, 70%, 75%, 80%, 85%, 90%, 95%, or 100% (reduced; abolished) following treatment with one or more RORC inhibitors (RORγ and/or RORγt inhibitors), relative to the area of the precancerous or cancerous lesions in the absence of or prior to treatment with an inhibitor of an RORC product.

In some embodiments, at least one topical inhibitor of an RORC product is administered (applied) in sufficient concentration and over sufficient to inhibit RORC product activity. By "inhibit RORC product activity", it is meant that RORγ and/or RORγt activity is less than it would be in the absence of at least one topical inhibitor of an RORC product. For example, the inhibitor reduces activity of RORγ and/or RORγt by at least 2%, 5%, 10%, 15%, 20%, 25%, 30%, 35%, 40%, 45%, 50%, 55%, 60%, 65%, 70%, 75%, 80%, 85%, 90%, 95%, or 100%.

Doses of RORC Inhibitor(s)

The concentration of RORC inhibitor(s) necessary may vary depending on the RORC inhibitor(s) used.

The concentration of RORC product inhibitor ("inhibitor") for an individual can range, for example, from 1 mg/ml inhibitor to 100 mg/ml inhibitor, from 10 mg/ml inhibitor to 100 mg/ml inhibitor, and can be determined using available methods known in the art. Concentration refers to the concentration of a single inhibitor (e.g., an RORγ inhibitor, an RORγt inhibitor, an inhibitor that inhibits both RORγ and RORγt); the concentration of a combination of inhibitors (e.g., a combination of more than one RORγ inhibitor; a combination of more than one RORγt inhibitor; a combination of one or more inhibitor of RORγ and one or more inhibitor of RORγt; a combination of inhibitors that inhibit both RORγ and RORγt); the concentration of a combination of RORC inhibitors (e.g., any combination of RORγ inhibitor(s), RORγt inhibitor(s), and inhibitors that inhibit both RORγ and RORγt). In those instances in which a combination of inhibitors is used, the concentration of each inhibitor can be 10 to 100 mg/ml or more, as needed or the concentration of all inhibitors in the combination (the combined concentration) can be 10 to 100 mg/ml or more, as needed. The concentration of RORC product inhibitor(s) in a composition applied to the skin of a subject in need thereof may be, for example, 1 mg/ml, 2 mg/ml, 3 mg/ml, 4 mg/ml, 5 mg/ml, 6 mg/ml. 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 22 mg/ml, 24 mg/ml, 26 mg/ml, 28 mg/ml, 30 mg/ml, 32 mg/ml, 34 mg/ml, 36 mg/ml, 38 mg/ml, 40 mg/ml, 42 mg/ml, 44 mg/ml, 46 mg/ml, 48 mg/ml, 50 mg/ml, 52 mg/ml, 54 mg/ml, 56 mg/ml, 58 mg/ml, 60 mg/ml, 62 mg/ml, 64 mg/ml, 66 mg/ml, 68 mg/ml, 70 mg/ml, 72 mg/ml, 74 mg/ml, 76 mg/ml, 78 mg/ml, 80 mg/ml, 82 mg/ml, 84 mg/ml, 86 mg/ml, 88 mg/ml, 90 mg/ml, 91 mg/ml, 92 mg/ml, 93 mg/ml, 94 mg/ml, 95 mg/ml, 96 mg/ml, 97 mg/ml, 98 mg/ml, 99 mg/ml, 100 mg/ml, or more. In some embodiments, the concentration of RORC product inhibitor(s) applied to the skin of a subject in need thereof may range from 1 mg/ml to 10 mg/ml, 10 mg/ml to 100 mg/ml, 20 mg/ml to 100 mg/ml, 30 mg/ml to 100 mg/ml, 40 mg/ml to 100 mg/ml, 50 mg/ml to 100 mg/ml, 60 mg/ml to 100 mg/ml, 70 mg/ml to 100 mg/ml, 80 mg/ml to 100 mg/ml, 90 mg/ml to 100 mg/ml, 10 mg/ml to 90 mg/ml, 20 mg/ml to 90 mg/ml, 30 mg/ml to 90 mg/ml, 40 mg/ml to 90 mg/ml, 50 mg/ml to 90 mg/ml, 60 mg/ml to 90 mg/ml, 70 mg/ml to 90 mg/ml, 80 mg/ml to 90 mg/ml, 10 mg/ml to 80 mg/ml, 20 mg/ml to 80 mg/ml, 30 mg/ml to 80 mg/ml, 40 mg/ml to 80 mg/ml, 50 mg/ml to 80 mg/ml, 60 mg/ml to 80 mg/ml, 70 mg/ml to 80 mg/ml, 10 mg/ml to 70 mg/ml, 20 mg/ml to 70 mg/ml, 30 mg/ml to 70 mg/ml, 40 mg/ml to 70 mg/ml, 50 mg/ml to 70 mg/ml, 60 mg/ml to 70 mg/ml, 10 mg/ml to 60 mg/ml, 20 mg/ml to 60 mg/ml, 30 mg/ml to 60 mg/ml, 40 mg/ml to 60 mg/ml, 50 mg/ml to 60 mg/ml, 10 mg/ml to 50 mg/ml, 20 mg/ml to 50 mg/ml, 30 mg/ml to 50 mg/ml, 40 mg/ml to 50 mg/ml, 10 mg/ml to 40 mg/ml, 20 mg/ml to 40 mg/ml, 30 mg/ml to 40 mg/ml, 10 mg/ml to 30 mg/ml, 20 mg/ml to 30 mg/ml, 10 mg/ml to 20 mg/ml, and 10 mg/ml to 15 mg/ml.

Administration of RORC Inhibitor(s)

Provided herein, in some embodiments, are methods of administering at least one dose of the RORC inhibitor(s) (RORγ inhibitor(s) and/or RORγt inhibitor(s)). In some embodiments, the RORC product inhibitor(s) may be administered repeatedly (repetitively). "Repeatedly" or "repetitive" dosing means at least one additional dose or dosing that is administered to a subject subsequent to an earlier dose or dosing of the same material. While the material may be the same, the amount of the material in the repeated dose may be different (e.g., more or less) from the earlier dose (e.g., comprise more or less RORC inhibitor(s) than the earlier dose).

In some embodiments, a dose of the RORC product inhibitor(s) may be administered on a schedule such as 1-5 times daily, twice a day, once a day, every other day, twice a week, once a week, once every two weeks, once every three weeks, once a month, once every two months or longer, and in any schedule combination thereof until the keratinocyte-derived malignancy (e.g., precancerous lesion or cancer lesion) is treated (e.g., for 1 week, 2 weeks, 3 weeks, 1 month, 2 months, 3 months, 4 months, 5 months, 6 months, 1 year, or longer). In some embodiments, the RORC inhibitor(s) may be applied to prevent or reduce the extent to which precancerous lesions or cancerous lesions occur on a schedule such as 1-5 times daily, twice a day, once a day, every other day, twice a week, once a week, once every two weeks, once every three weeks, once a month, once every two months or longer, and in any schedule combination thereof. In some embodiments, the RORC product inhibitor(s) may be administered on an as-needed basis, preventatively and/or therapeutically, to a subject in need thereof.

In embodiments in which RORC inhibitor(s) (RORγ inhibitor(s) and/or RORγt inhibitor(s)) are applied in order to reduce or prevent development of precancerous or cancerous lesions in an individual in need thereof, RORC inhibitor(s) are applied, for example, at the time exposure to the sun begins or prior to sun exposure, such as 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 12 hours, or one day prior to UV exposure (e.g., UVB exposure). In some embodiments, the RORC inhibitor(s) (RORγ inhibitor(s) and/or RORγt inhibitor(s)) are applied in order to reduce or prevent development of precancerous or cancerous lesions in an individual in need thereof, RORC inhibitor(s) are applied, for example, at the time exposure to the sun begins or prior to sun exposure, such as 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 12 hours, 1 day, 2 days, 3 days, 4 days, 5 days, 6 days, 1 week, or 2 weeks after UV exposure (e.g., UVB exposure). In some embodiments, the RORC inhibitor(s) (RORγ inhibitor(s) and/or RORγt inhibitor(s)) may be administered both prior to and following UV exposure (e.g., UVB exposure). In some embodiments, the RORC inhibitor(s) (RORγ inhibitor(s) and/or RORγt inhibitor(s)) are administered daily or twice daily (morning and evening), or immediately prior to or immediately after sun (or other sources of ultraviolet radiation) exposure.

In the case of a relapse or insufficient or incomplete therapeutic effect, dosing can be re-initiated.

Formulations

The RORC inhibitor(s) (RORγ inhibitor(s) and/or RORγt inhibitor(s)) may be formulated for topical administration (e.g., administration to the skin of a subject) using a vehicle or carrier that promotes the penetration of RORγ and/or RORγt inhibitors through the stratum corneum and into the viable epidermal cells (e.g. keratinocytes) and dermal cells. Examples of topical formulations include solutions and sprays, gels, ointments, creams, lotions, pastes, foams, and patches. In some embodiments, anhydrous gels, and hydrous gels, or polymer-assisted delivery (e.g., with PLA-based nanoparticles or micronized particles) may be used to deliver the RORC inhibitor(s) (RORγ inhibitor(s) and/or RORγt inhibitor(s)) to the subject. Methods of generating a formulation are known in the art. As one example, the RORC inhibitor(s) (RORγ inhibitor(s) and/or RORγt inhibitor(s)) may be formulated into a solution, such as with ethanol and water (e.g., 60% ethanol, 40% water). In some embodiments, the percentage of the RORC inhibitor(s) (RORγ inhibitor(s) and/or RORγt inhibitor(s)) within a formulation is 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more. In certain embodiments, 0.1% to 10%, such as 1% inhibitor(s), are present in a cream preparation (100 micromolar range).

As described herein, application of 1% inhibitor (in 60% ethanol and 40% water) over 4 $cm^2$ skin area daily for 2 weeks was found to be sufficient to decrease mutant keratinocyte clonal area by 60% (FIG. 3A).

The RORC inhibitor (RORγ inhibitor(s) and/or RORγt inhibitor(s)) formulation may be applied directly to the desired area of the skin or with an applicator, such as a cotton-tipped swab.

Combination Therapy

In some embodiments, the RORC inhibitor(s) (RORγ inhibitor(s) and/or RORγt inhibitor(s)) are administered with other agents, for example, agents that reduce or minimize skin cancer risk. Examples of such agents include, but are not limited to sunscreen/sunblock (physical and organic UV filters), anti-oxidants (to prevent the generation of reactive oxygen species; e.g., triplet-state preventers (TSPs) or triple-state quenchers (TPQs)), anti-aging agents, and anti-inflammatory agents. The agents may be applied prior to, concurrently (simultaneously, concomitantly) with, or following application of the RORC inhibitor(s) (RORγ inhibitor(s) and/or RORγt inhibitor(s)). The additional agents can be applied to the skin or administered by another route (e.g., orally or intravenously).

For example, a further aspect of the disclosure provides methods and compositions relating to treating or preventing skin aging, cellular/DNA damage to skin, and/or skin cancer with a composition described herein and a second agent. Such compositions may be useful, for example, to prevent skin aging (e.g., wrinkling) or skin cancer, or to reduce the extent or delay the onset of either condition. In some embodiments, the methods include the repetitive topical application of compositions comprising RORC inhibitor(s) (RORγ inhibitor(s) and/or RORγt inhibitor(s)) and one or more additional agents, such as anti-oxidants, anti-tumor promoting growth factors, CYP1B1 inhibitors, or any combination thereof.

Examples of anti-oxidants include, but are not limited to, natural/herbal antioxidants (e.g., curcumin, lycopene, lutein, alpha-lipoic acid), vitamins and their derivatives, (e.g. ascorbic acid (vitamin C), vitamin A, vitamin B3, vitamin E, beta-carotene), minerals (e.g. selenium, zinc), polyphenols (e.g. soy-derived genistein), dietary agents/supplements (e.g. resveratrol), retinols and retinoids, and enzymes (e.g. superoxide dismutase (SOD), catalase (CAT), glutathione peroxidase (GSHpx), glutathione reductase, and nitric oxide synthases (NOS-1, -2, -3)).

Examples of anti-tumor promoting growth factors include, but are not limited to, inhibitors of epidermal growth factors (e.g. epidermal derived growth factors (EDGF), keratinocyte growth factors (KGF), insulin-like growth factors (IGF)), and inhibitors of tumor-promoting cytokines (e.g. interleukin-22, GRO-1, AREG).

Examples of CYP1B1 inhibitors include, but are not limited to, direct and specific inhibitors of CYP1B1, CYP1A1, and other metabolizing agents that detoxify active mutagens/carcinogens, general inhibitors of P450 enzymes, and inhibitors and/or agonists of the aryl hydrocarbon receptor (AHR).

In some embodiments, one or more anti-tumor promoting growth factors and/or CYP1B1 inhibitors are administered via a nanocarrier (e.g., bioadhesive nanoparticles, BNPs).

In some embodiments, the RORC inhibitor(s) (RORγ inhibitor(s) and/or RORγt inhibitor(s)) are applied with one or more sunscreen filter agents (e.g., physical and organic UV filters). In some embodiments, the RORC inhibitor(s) (RORγ inhibitor(s) and/or RORγt inhibitor(s)) are administered (applied) with one or more sunscreen filter agents and one or more anti-oxidants. In some embodiments, the RORC inhibitor(s) (RORγ inhibitor(s) and/or RORγt inhibitor(s)) are administered with one or more sunscreen filter agents and one or more anti-tumor promoting growth factors. In some embodiments, the RORC inhibitor(s) (RORγ inhibitor(s) and/or RORγt inhibitor(s)) are administered with one or more sunscreen filter agents and one or more CYP1B1 inhibitors. In some embodiments, the RORC inhibitor(s) (RORγ inhibitor(s) and/or RORγt inhibitor(s)) are administered with at least two additional agents selected from the group consisting of: anti-oxidants, anti-tumor promoting growth factors, and CYP1B1 inhibitors.

In some embodiments, the RORC inhibitor(s) (RORγ inhibitor(s) and/or RORγt inhibitor(s)) are administered to a subject receiving one or more anti-cancer therapies and/or one or more radiation therapies. Examples of anti-cancer therapies used for skin cancer include, but are not limited to, surgery (e.g., simple excision, Mohs micrographic surgery, shave excision, curettage and electrodesiccation, cryosurgery, laser surgery, or dermabrasion), radiation (e.g., external radiation therapy, internal radiation therapy), chemotherapy, photodynamic therapy, immunotherapy, targeted therapy (e.g., vismodegib, sonidegib), chemical peel, and other drug therapies (e.g., retinoids, diclofenac, ingenol).

Subjects

The methods and compositions described herein may be used to treat a subject having skin cancer or at risk of having skin cancer. "Subject" includes animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like. In any one of the methods and compositions provided herein, the subject is human.

Subjects at a higher risk for pre-cancer and skin cancer include those having fair skin (e.g., Fitzpatrick type 1, 2, or 3), those having an MC1R deficiency (e.g., red hair, freckles), or other fair skin states (e.g., blonde hair, blue eyes). Other risk factors for skin cancer include a personal and/or family history of pre-cancerous or skin cancerous lesions and genetic polymorphisms (e.g., those that increase the risk of melanoma, such as MC1R, CDKN2A0MTAP, PLA2G6, TERT, TYR, MC1R, SLC45A2, ASIP; those that increase the risk of basal cell carcinoma, TYR, MC1R, PTCH1, PTCH2, SUFU, MYCN, ZFHX4, CASP8, GATA3; and/or that increase the risk of squamous cell carcinoma, TYR, MC1R, IRF4, CTLA4, DEF8, XRCC1, UBAC2, EXOC2). In addition, genetic disorders such as basal cell nevus syndrome, xeroderma pigmentosum, epidermolysis bullosa, or oculocutaneous albinism, and familial atypical mole-melanoma syndrome (FAM-M syndrome) also increase a subject's risk of skin cancer. Subjects at a greater risk for skin cancer also include those with iatrogenic disorders of immune suppression, for example, pharmacologically rendered for prevention of organ transplantation rejection (e.g. with tacrolimus, cyclosporine A, rapamycin, mycophenolate), after peripheral blood stem cell transplantation, or for the treatment of autoimmune disorders. Finally, subjects who have substantial prior (UV-induced) photodamage (e.g. for treatment of prior malignancy, or via accidental or occupational exposure), or chemical/mutagenic exposure (e.g., industry exposures and smoking) may be at an increased risk of skin cancer. Clinical indices of increase risk include, but are not limited to, clinical evidence of lentigines, ephylides, telangiectasias, and rhytidides.

Further Embodiments

In further embodiments, the RORC inhibitor(s) (RORγ inhibitor(s) and/or RORγt inhibitor(s)) may administered with agents that are not RORC inhibitor(s) to treat or prevent, for example, cutaneous inflammatory states or diseases or follicular diseases, as described below.

For example, a further aspect of the disclosure provides methods and compositions relating to topical formulations of anti-inflammatory agents. In some embodiments, the RORC inhibitor(s) (RORγ inhibitor(s) and/or RORγt inhibitor(s)) described herein are administered with anti-inflammatory agents to target cutaneous inflammation in order to prevent or treat (e.g., reduce the severity or delay the onset of) an inflammatory skin disease. Examples of inflammatory skin diseases include, but are not limited to, atopic dermatitis, allergic contact dermatitis (e.g. poison ivy), psoriasis, dermatitis NOS (e.g., irritant dermatitis), cutaneous lupus erythematosus, vitiligo, and alopecia areata. Examples of anti-inflammatory agents include, but are not limited to, corticosteroids, non-steroidal anti-inflammatory drugs (NSAIDS) (e.g. aspirin, ibuprofen), Jak and/or Stat inhibitors, and Dapsone.

In another aspect, the disclosure provides methods and compositions relating to topical formulations for the prevention or treatment of follicular disorders, such as acne or alopecia. In some embodiments, the compositions and methods include the repetitive topical application of RORC inhibitor(s) (RORγ inhibitor(s) and/or RORγt inhibitor(s)) with one or more anti-acne agents for prevention and/or of treatment of acne vulgaris, hidradenitis suppurativa, folliculitis decalvans, or dissecting folliculitis. Examples of anti-acne agents include, but are not limited to, benzoyl peroxide, retinoids (including tretinoin), Dapsone, and TNF-alpha inhibitors, and other anti-inflammatory agents (e.g., those described above).

In some embodiments, the compositions and methods include the repetitive topical application of RORC inhibitor(s) (RORγ inhibitor(s) and/or RORγt inhibitor(s)) with one or more hair growth stimulation agents to treat alopecia-causing conditions, such as androgenetic alopecia, alopecia areata, traction alopecia, scarring alopecia, and lichen planopilaris. Examples of hair growth stimulation agents include, but are not limited to, growth factors (including fibroblast growth factors (FGFs), keratinocyte growth factors (KFG), and epidermal-derived growth factors (EDGF)), inhibitors of the dihydrotestosterone (DHT) receptor and other hormones and hormone receptors, and anti-inflammatory agents (including TNF-alpha inhibitors, NSAIDs, Jak and/or Stat inhibitors, and NKG2D inhibitors).

The present disclosure encompasses at least the following additional embodiments:

The present disclosure, provides in some aspects, a method of inhibiting (partially or completely) development of keratinocyte-derived malignancy characterized by mutations in p53 gene, comprising applying repetitively at least one topical inhibitor of an RORC product to skin in sufficient concentration and over sufficient time to reduce local production of at least one factor that drives keratinocyte transformation and mutant clonal expansion. In some embodiments, the at least one factor is IL-17A, IL-17F, IL-22 or IL-36a.

Aspects of the present disclosure include a method of inhibiting UVB-induced cutaneous carcinogenesis, comprising applying topically and repetitively to skin at least one inhibitor of RORγ or at least one inhibitor of RORγ-t in sufficient concentration and for sufficient length of time to inhibit keratinocyte genotoxicity, epidermal proliferation and dedifferentiation and mutant p53 keratinocyte clonal expansion.

Another aspect of the present disclosure includes a method of inhibiting actinic keratosis and squamous cell carcinoma in an individual, comprising applying repetitively at least one topical inhibitor of an RORC product to the individual's skin in sufficient concentration and over sufficient time to reduce (partially or completely) UVB-induced cutaneous carcinogenesis.

In some embodiments of any of the methods described herein, the concentration of RORγ inhibitors, RORγt inhibitors or combinations of RORγ inhibitors and RORγt inhibitors is from about 10 mg/ml to about 100 mg/ml or about 1% inhibitor (in solution, e.g. 60% ethanol, 40% water, or other topical formulations including cream, ointment, foam, sprays, and gels; including anhydrous and hydrous) and the at least one topical inhibitor is applied repeatedly, including once monthly (for at least 4 months), weekly (for at least 4 weeks), or daily.

Some aspects of the disclosure provide a composition comprising at least one RORγ inhibitor, at least one RORγt inhibitor or a combination of at least one RORγ inhibitor and at least one RORγt inhibitor at a concentration of from about 10 mg./ml. to about 100 mg./ml. or about 1% (in solution, e.g. 60% ethanol, 40% water, or other topical formulations including cream, ointment, foam, sprays, and gels; including anhydrous and hydrous). In some embodiments, the composition described herein further comprises at least one of the following: an anti-oxidant, a sunscreen filter agent, an anti-aging agent, an anti-inflammatory agent and a triplet state preventer and a triplet state quencher.

EXAMPLES

RORγ and/or RORγt Targeting for Prevention of Skin Cancer

Skin cells from B6.TCRβ-/-δ-/- mice after UVB light exposure and in the presence of Langerhans cells (NLC) were isolated and screened for different immune cell differentiation factors. As FIGS. 1A-1C demonstrate, it was determined that expression of RORC and its cytokine products (IL-22 and IL-17) were significantly elevated relative to other immune cell differentiation factors tested.

Further characterization was performed, and it was found that RORC+ skin innate lymphoid cells (ILC) were CD103+ and ICOS+ (FIG. 2A) and that IL-22- and IL-17A-positive cells are intracellular CD3e+ (FIG. 2B). Intracellular CD3e+ cells were found in chronic UVB exposed epidermis (FIG. 2C), and, in RORγt-deficient mice, it was found that epidermal EGFP+ cells were largely intracellular CD3e+ (FIG. 2D). Therefore, RORγt-deficient mice do not expand their mutant keratinocyte clones induced by ultraviolet light (sunlight). These clones remain as minute remnants. It was determined that the key skin immune cells were RORγt+ Sca-1+CCR6+ICOS+CD2+/-.

As shown in FIGS. 3A and 3B, application of RORCi, an inhibitor of RORγ and RORγt, markedly decreased mutant keratinocyte clonal expansion and repressed expression of key cytokines and growth factors produced by RORC+ immune cells in mice after exposure to UVB. RORCi was administered daily for two weeks over 4 cm$^2$ of skin in a solution of 1% inhibitor (in 60% ethanol and 40% water). FIG. 3A demonstrates that mutant keratinocyte levels were reduced 60% in the skin.

What is claimed is:

1. A method of inhibiting development of a keratinocyte-derived malignancy characterized by mutations in a p53 gene, the method comprising applying repetitively a topical inhibitor of an RAR-related orphan receptor C (RORC) product to skin of an individual in need thereof in sufficient concentration and over sufficient time to inhibit RORC product activity, wherein the topical inhibitor inhibits (i) RORγ, (ii) RORγt, or (iii) RORγ and RORγt.

2. The method of claim 1, wherein the topical inhibitor is applied repetitively in sufficient concentration and over sufficient time to reduce local production of a factor that drives keratinocyte transformation or mutant clonal expansion.

3. The method of claim 2, wherein the factor is selected from the group consisting of: IL-17A, IL-17F, IL-22, and IL-36a.

4. The method of claim 1, wherein the keratinocyte-derived malignancy is selected from the group consisting of: cutaneous carcinogenesis, squamous cell carcinoma, basal cell carcinoma, Merkel cell carcinoma, and actinic keratosis.

5. A method of inhibiting UV-induced cutaneous carcinogenesis, the method comprising applying repetitively a topical inhibitor of an RORC product to skin of an individual in need thereof in sufficient concentration and for sufficient length of time to inhibit keratinocyte genotoxicity, epidermal proliferation and dedifferentiation, mutant p53 keratinocyte clonal expansion, or any combination of two or more thereof, wherein the topical inhibitor inhibits (i) RORγ, (ii) RORγt, or (iii) RORγ and RORγt.

6. A method of inhibiting actinic keratosis and squamous cell carcinoma, the method comprising applying repetitively a topical inhibitor of an RORC product to skin of an individual in need thereof in sufficient concentration and for sufficient length of time to inhibit UV-induced cutaneous carcinogenesis, wherein the topical inhibitor inhibits (i) RORγ, (ii) RORγt, or (iii) RORγ and RORγt.

7. The method of claim 1, wherein the topical inhibitor is selected from the group consisting of: ML209, RORCi, digoxin, ursolic acid, SR1001, SR2211, TMP778, VPR-66, GSK805, and CSK2981278.

8. The method of claim 1, wherein two or more topical inhibitors of an RORC product are administered to the skin.

9. The method of claim 1, wherein two or more topical inhibitors that inhibit RORγ are administered to the skin.

10. The method of claim 1, wherein two or more topical inhibitors that inhibit RORγt are administered to the skin.

11. The method of claim 1, wherein two or more types of topical inhibitors that inhibit RORC products selected from the group consisting of: (i) topical inhibitors that inhibit RORγ, (ii) topical inhibitors that inhibit RORγt, and (iii) topical inhibitors that inhibits RORγ and RORγt are administered to the skin.

12. The method of claim 1, wherein the topical inhibitor is administered twice daily.

13. The method of claim 1, wherein the topical inhibitor is administered once daily.

14. The method of claim 1, wherein the topical inhibitor is formulated in a composition comprising a gel, an ointment, a cream, a foam, a spray, or a solution.

15. The method of claim 14, wherein the composition comprises about 1% of the topical inhibitor.

16. The method of claim 1, further comprising applying an anti-skin cancer agent selected from the group consisting of: sunscreen, anti-oxidants, anti-aging agents, and anti-inflammatory agents to the skin.

* * * * *